United States Patent
Seth (10) Patent No.: US 11,730,187 B2
(45) Date of Patent: Aug. 22, 2023

(54) USE OF ISOTHIOCYANATE IN SMOKELESS TOBACCO PRODUCTS

(71) Applicants: Avinash Seth, Pomona, CA (US); GAMOT GLOBAL PTE. LTD., Singapore (SG)

(72) Inventor: Avinash Seth, Pomona, CA (US)

(73) Assignee: Gamot Global PTE. LTD., Singapore (SG)

(*) Notice: Subject to any disclaimer, the term of this patent is extended or adjusted under 35 U.S.C. 154(b) by 370 days.

(21) Appl. No.: 16/868,830

(22) Filed: May 7, 2020

(65) Prior Publication Data

US 2020/0352215 A1 Nov. 12, 2020

Related U.S. Application Data

(60) Provisional application No. 62/844,846, filed on May 8, 2019.

(51) Int. Cl.
| | |
|---|---|
| *A24B 15/30* | (2006.01) |
| *A61K 36/23* | (2006.01) |
| *A61K 36/31* | (2006.01) |
| *A61K 31/26* | (2006.01) |
| *A61K 38/47* | (2006.01) |
| *A24B 15/28* | (2006.01) |
| *A61K 31/375* | (2006.01) |
| *A61K 31/05* | (2006.01) |
| *A24B 15/40* | (2006.01) |
| *A61K 31/122* | (2006.01) |

(52) U.S. Cl.
CPC .......... *A24B 15/303* (2013.01); *A24B 15/283* (2013.01); *A24B 15/301* (2013.01); *A24B 15/406* (2013.01); *A61K 31/05* (2013.01); *A61K 31/122* (2013.01); *A61K 31/26* (2013.01); *A61K 31/375* (2013.01); *A61K 36/23* (2013.01); *A61K 36/31* (2013.01); *A61K 38/47* (2013.01)

(58) Field of Classification Search
CPC ...... A61K 31/05; A61K 31/122; A61K 31/26; A61K 31/325
See application file for complete search history.

(56) References Cited

U.S. PATENT DOCUMENTS

| | | | |
|---|---|---|---|
| 6,845,777 B2 | 1/2005 | Pera | |
| 9,593,077 B2 | 3/2017 | Payne | |
| 2003/0084912 A1 | 5/2003 | Pera | |
| 2003/0235634 A1 | 12/2003 | Pusateri et al. | |
| 2008/0017207 A1 | 1/2008 | Dev et al. | |
| 2010/0178286 A1 | 7/2010 | Smith | |
| 2015/0068544 A1 | 3/2015 | Moldoveanu et al. | |

FOREIGN PATENT DOCUMENTS

| | | | |
|---|---|---|---|
| CA | 2 866 912 | 8/2016 | |
| CN | 101120948 A | 2/2008 | |
| CN | 101406319 | 4/2009 | |
| CN | 104872685 | 9/2015 | |
| CN | 106900962 | 6/2017 | |
| DE | 202008005433 | 4/2009 | |
| EP | 3295794 | 3/2018 | |
| WO | 0061163 | 10/2000 | |
| WO | 2006075330 | 7/2006 | |
| WO | 2009/015142 | 1/2009 | |
| WO | WO-2009115160 A2 * | 9/2009 | ............ A23G 4/068 |
| WO | 2011112919 | 9/2011 | |
| WO | 2012142511 | 10/2012 | |
| WO | 2016100430 | 6/2016 | |

OTHER PUBLICATIONS

Ramaswamya, Suvasini, et al. "Systemic delivery of factor IX messenger RNA for protein replacement therapy," Laboratory of Genetics, Salk Institute for Biological Studies, La Jolla, CA. 10 pages.
Bo et al., Duration of Nicotine Replacement Therapy Use and Smoking Cessation: A Population-Based Longitudinal Study, American J Epi, vol. 181, No. 7, 2015, 513-520).
Ko et al., The Role of Resveratrol in Cancer Therapy: International Journal of Molecular Studies; Published1 Dec. 2017; pp. 1-36.
Extended European Search Report for European Patent Appln. No 20801799.6-1105, dated Dec. 6, 2022, 11 pages.
International Search Report in corresponding African Application No. AP/P/2021/013605, dated Jun. 21, 2023, 2 pages.
Parveen et al., "Phytochemicals Targeting VEGF and VEGF-Related Multifactors as Anticancer Therapy," J. Clin. Med., Mar. 12, 2019, 39 pages, vol. 8, No. 350.

* cited by examiner

*Primary Examiner* — Kevin E Weddington
(74) *Attorney, Agent, or Firm* — Fish IP Law, LLP (57) ABSTRACT

A tobacco product reduces or mitigates some of the negative effects of tobacco consumption, particularly cancer development. The tobacco product contains (a) nicotine, (b) at least one of an isothiocyanate or isothiocyanate precursor, (c) myrosinase and (d) a synthetic isothiocyanate. The product can further include at least one of thymoquinone, resveratrol, synthetic vitamin C, thymoquinone resveratrol and a synthetic vitamin C.

21 Claims, 5 Drawing Sheets

FIGURE 1
CELLS AND DMSO CONTROL

FIGURE 2
AITC

RESVERATROL

PEITC 25µM / AITC 25µM / TQ 25µM

FIGURE 8

TQ 50µM / RSV 50 µM

FIGURE 9

USE OF ISOTHIOCYANATE IN SMOKELESS TOBACCO PRODUCTS

The present application claims the benefit of, and priority to, Provisional Patent Application Ser. No. 62/844,846 filed on May 8, 2019, titled "Use Of Isothiocyanate In Smokeless Tobacco Products", which is hereby incorporated fully by reference into the present application.

FIELD OF THE INVENTION

The field of the invention is a tobacco product for reducing the negative effects of tobacco consumption.

BACKGROUND

The background description includes information that may be useful in understanding the present invention. It is not an admission that any of the information provided herein is prior art or relevant to the presently claimed invention, or that any publication specifically or implicitly referenced is prior art.

In 2017, 14 of every 100 U.S. adults aged 18 years or older (14.0%) currently smoke cigarettes. This means that an estimated 34 million adults in the US currently smoke cigarettes. More than 16 million Americans live with a smoking-related disease. According to the Office on Smoking and Health, cigarette smoking causes more than 480,000 deaths every year in the US and this is nearly one in five deaths in the US.

Smokers are more likely than nonsmokers to develop lung cancer. For example, smoking men and women develop lung cancer by 25 times more than non-smoking men and women. According to the American cancer society, tobacco smoke is made up of thousands of chemicals, including at least 70 known to cause cancer (carcinogen) such as acetaldehyde, acrylonitrile, formaldehyde, lead, N-Nitorsopiperidine, and vinyl chloride. It is well-known that smoking can cause cancer almost anywhere in our body including bladder, blood, cervix, colon, esophagus, kidney, ureter, larynx, liver, oropharynx, pancreas, stomach, trachea, bronchus, and lung.

Many smokers are eager to quit smoking, however, it is very difficult due to nicotine addiction. Nicotine is a drug that occurs naturally in tobacco, and is thought to be as addictive as heroin or cocaine. Smokers suffer physical and emotional withdrawal symptoms when they stop smoking. One of the common ways to treat nicotine addiction is the use of Nicotine Replacement Therapy (NRS), such as nicotine patches and nicotine gum. In a 2015 study about people who were trying to quit smoking using NRS, about 20% of smokers in the control group quit smoking. On the other hand, about 52% of people who used NRS for at least 2 months, managed to quit smoking (Bo et al., American J Epi, 2015, 513-520). This result indicates that NRS effectively works for smokers who want to quit smoking. On the other hand, almost 50% of smokers in the study failed to quit smoking, even though they used NRS. In addition, there are many smokers who do not even try to quit smoking due to the significant effort and time required for quitting.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Some smokers use a cigarette substitute to quit smoking. Even though the cigarette substitute does not contain nicotine, it might reduce the cigarette craving due to the simple motor effects of smoking behavior. CA2866912 teaches a cigarette substitute where the substitute contains isothiocyanate. Isothiocyanate works as an anti-cancer agent in cancer cells including lung, breast and oral cancer cells. It helps to prevent or reduce cancer development when smokers continuously use the substitute. However, many smokers still return to smoke a real tobacco product because of nicotine craving.

WO2009/05142A2 teaches a smokeless tobacco product containing isothiocyanate to prevent and/or reduce cancer development in smokers. As described above, isothiocyanate works as an anti-cancer agent. Therefore, smoking this tobacco product is likely less harmful with respect to cancer development as compared to other smokers, but still more harmful that with respect to non-smokers.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Thus, there is still a need for a tobacco product having increased effectiveness for reducing the negative effects of tobacco consumption.

SUMMARY OF THE INVENTION

The inventive subject matter provides apparatus, systems and methods for a tobacco product having increased effectiveness for reducing the negative effects of tobacco consumption.

An ingestible product, for example, a smokeless tobacco, a chewing tobacco, a snuff, a snus, a dissolvable tobacco, a cigarette, a twist, a cigar, and a cigarillo, includes nicotine, at least one of isothiocyanate or an isothiocyanate precursor, and myrosinase.

The nicotnine can be derived from at least one of powdered tobacco leaf and a tobacco leaf extract. The isothiocyanate precursor can be derived from at least one of water cress, water cress extract, garden cress, and garden cress extract. The isothiocyanate can be synthetic. The myrosinase can be derived from at least one of mustard seed and mustard seed extract. The ingestible product can further include at least one of thymoquinone, a black, cumin seed extract, resveratrol and a synthetic vitamin C.

In some embodiments, the ingestible product includes at least one of powdered tobacco leaf and a tobacco leaf extract as a source of the nicotine, and at least one of water cress, water cress extract, garden cress, and garden cress extract as a source of the isothiocsyanate precursor; and mustard seed extract as a source of the myrosinase. The ingestible product can further include synthetic isothiocyanate, thymoquinone, resveratrol, synthetic vitamin C, thymoquinone and a synthetic vitamin C.

In some embodiments, the nicotine and the isothiocyanate precursor in both or in each can be encapsulated and included in the ingestible product. The encapsolation can be formed by using at least one of micelles and nano-particles. In some embodiments, at least some of the isothiocyanate precursor can be in direct contact with at least one of powdered tobacco leaf and a tobacco leaf extract. The ingestible product can contain a filter.

20. A method of preventing or treating cancer in a population, but making available to at least some members of the population an ingestible product comprising nicotine, at least one of isothiocyanate and an isothiocyanate precursor, and myrosinase.

The inventive subject matter further includes a method of preventing or treating cancer in a population, but making available to at least some members of the population an ingestible product including nicotine, at least one of isothiocyanate and an isothiocyanate precursor, and myrosinase.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values herein is merely intended to serve as a shorthand method of referring individually to each separate value falling within the range. Unless otherwise indicated herein, each individual value is incorporated into the specification as if it were individually recited herein.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The tobacco products contemplated herein are referred to as being "ingestible" because either (a) they are retained in the mouth such that juices emanating from the product are swallowed, or (b) they are smoked or vaped, such that inhaled components are mixed with saliva and then swallowed. Such ingestible product includes at least one of the following: smokeless tobacco, tobacco leaf extract, chewing tobacco, snuff, snus, dissolvable tobacco, cigarette, twist, a cigar, and cigarillo.

Preferred embodiments contain (a) nicotine, (b) at least one of isothiocyanate or isothiocyanate precursor, and (b) myrosinase. The nicotine can be derived from any suitable source of nicotine, for example, powdered tobacco leaf and/or tobacco leaf extract.

Isothiocyanate (ITC), R—N=C=S a well known anti-cancer molecule, increasing p53 expression, depleting mutant p53 expression, inducing mitotic cell cycle arrest and apoptosis in cancer cells including breast, lung, and cancer cell lines. As used herein, the term ITC includes isothiocyanate analogs and a precursor of ITC, provided such molecules increase p53 expression, deplete mutant p53 expression, induce mitotic cell cycle arrest and apoptosis in cancer cells. ITC analogs include Allyl ITC (AITC), Phenethyl ITC (PEITC), and Benzyl ITC (BITC) which are derived from cruciferous vegetables (37). In some embodiments, the vegetables and/or vegetable extracts can be added to the ingestible product.

A precursor of ITC, ethyl glucosinolate (PEGLS), derived from watercress and/or watercress extract, can be hydrolyzed enzymatically into PEITC (4). Myrosinase, an endogenously or exogenously obtained enzyme, can be used to hydrolyze glucosinolates. Other precursors of ITC include glucotropaeolin for BITC, gluconasturtiin for PEITC, and Allyl Glucosinolate (Sinigrin) for AITC, and can all be enzymatically converted to ITC. Other sources of the precursor ITC include garden cress and garden cress extracts that are rich in Glucotropaeolin.

In some embodiments, watercress, its extract, garden cress and/or its extract can be added to provide the ITC precursor, and an endogenous and/or exogenous myrosinase can be added to facilitate the hydrolysis to ITC. Additionally or alternatively an ingestible product can include a purified ITC.

Myrosinase can be derived from at least one of mustard seed and mustard seed extract. In some embodiments, the mixture of the watercress extract (source of PEGLC) and mustard seed extract (source of myrosinase) can be added to the ingestible product possibly generating PEITC. In another embodiment, the reactant (ex. PEITC) can be directly added to the ingestible product. In some embodiments, ITC can also be synthesized, and added directly to the ingestible product.

In some embodiments, the product further includes at least one of thymoquinone and a vitamin C. Thymoquinone can be extracted from Nigella sativa (black cumin seed) or other plant. Thymoquinone exhibits anticancer activity, showing inhibition of metastatic capacity (25), maintaining antioxidant activity, including preservation of anti-oxidant enzyme capacities such as glutathione peroxidase, catalase, and glutathione-S-transferase (7,26), and upregulation of p53 expression (28) in cancer cells including lung and breast cancer cells. Extracted or purified thymoquinone and/or the extract of the plant can be added to the ingestible product.

Resveratrol, a natural stilbene and a non-flavonoid polyphenol, is a phytoestrogen that possesses anti-oxidant, anti-inflammatory, cardioprotective, and anti-cancer properties (Ko et al., the role of Resveratrol in cancer therapy, Int J. Mo. Sci., 2017). It has been reported that resveratrol can reverse multidrug resistance in cancer cells, and, when used in combination with clinically used drugs, it can sensitize cancer cells to standard chemotherapeutic agents. Several novel analogs of resveratrol have been developed with improved anti-cancer activity, bioavailability, and pharmacokinetic profile.

Vitamin C also exhibits anticancer activity, showing upregulation of P53 expression (35). The vitamin C can be extracted from citrus fruits and can be added to the ingestible product.

The synergistic anti-cancer activity is expected by any combination of ITC, thymoquinone, resveratrol and vitamin C presented in the ingestible product and the results of the synergistic effect are shown in the figures below.

In some embodiments, a smokable product contains no nicotine, tobacco leaf or tobacco leaf extract, but does contain at least one of ITC, thymoquinone, resveratrol and vitamin C. And instead of tobacco leaf or a tobacco leaf extract, the smokable product includes a nicotine-free plant leaf, or extract, such as one or more nicotine-free herbs. Such product is nicotine-free, with anti-cancer activity, and as such it is contemplated current smokers as well as potential smokers could enjoy smoking the product.

In some embodiments, at least one of the nicotine, ITC, myrosinase, thymoquinone, resveratrol and vitamin C is encapsulated, and such encapsulation provides ingredients physically or chemically separated, entrapped, or suspended in the ingestible product. The encapsulation provides at least two advantages. First, it prevents molecular degradation and/or deformation from any acid produced from the tobacco leaf or extract. Second, a user can fully enjoy the taste of the ingestible product even though the product contains other materials in addition to the tobacco leaf or extract.

The encapsulation may include binders and/or surfactants. Examples of the binders are dicalicium phosphate, magnesium stearate, croscarmellose sodium, titanium dioxide, silica, parabens, lactose, maldodextrin, monodosium glutamate, talc, miscrocrystalline cellulose, gelatin, gellan gum, tartrazine, allura red, indigotine, indigotine, Polyvinylpyrrolidone, and sodium stearyl fumarate, stearic acid.

Surfactants are classified as anionic or nonionic. Contemplated surfactants for the subject matter herein are non-toxic, including palmitic acid, stearic acid and oleic acid (C16-C24) fatty acids, long chain (C16-C24) esters of fatty acids, polyethylene glycol, polyethylene glycol alkyl ethers, polyethylene glycolate mono- or di-fatty acid esters of polyethylene glycol, fatty acid mono, polyoxyethylene mono- and di-stearate, and polyoxyethylene ether, polyoxyethylene sorbitan monolaurate, monopalmitate, monostearate or monoesters, polyoxyethylene alkyl phenols and alkyl phenyl ethers, polysorbate, stearylamine, triethanolamine oleate, vegetable oils, polyoxyethylene very caillou, sorbitan fatty acid esters, and cholesterol.

The encapsulation can be micelles, microparticles, and nanoparticles. The micelles are formed using for examples, phospholipid, glycolipids, and Ionized fatty acids.

Examples of suitable materials for microparticles and nanoparticles are silica, alumina, titania, carbon black, aluminum silicate, calcium silicate, magnesium silicate, potassium silicate, sodium silicate, sodium aluminosilicate, sodium calcium aluminosilicate containing, tricalcium silicate, silica airgel, talc, iron oxide, other metal oxides combinations thereof.

A method of preventing or treating cancer in a population such as smokers provides an ingestible product containing nicotine, at least one of ITC and an ITC precursor, and myrosinase. The nicotine can be derived from at least one of powdered tobacco leaf and a tobacco leaf extract. The ITC can be derived from at least one of watercress, watercress extract, garden cress, and garden cress extract. The myrosinase can be derived from mustard seed extract. In some embodiments, the ingestible product further contains at least one of molecules including thymoquinone, resveratrol and vitamin C. The product can be packaged in any suitable form, including at least one of a smokeless tobacco, a chewing tobacco, a snuff, a snus, and a dissolvable tobacco, a cigarette, a twist, a cigar, and a cigarillo.

In contemplated experiments, the effect of the ingestible product could be examined in breast cancer cell (MCF7), Hela cells, oral cancer cells, A549 (human lung cancer cells). Cells are plated equal number and incubated with ITC, thymoquinone, and vitamin C individually and the combination thereof. The apoptosis progression could be measured using flow cytometry, and immunostaining against proteins that are responsible for apoptosis, such as TUNEL and caspase-3. Expression levels of wildtype and mutant p53 could be determined by qRT-PCR and immunostaining against wildtype and mutant p53. The cell cycle arrest at G2/M could be observed applying immunostaining against G2-M checkpoint regulators such as cyclin B1 and cdc2.

The cells could be divided into several groups including 1. No treatment, 2. ITC only, 3 thymoquinone only, 4 vitamin C only, 5 resveratrol only 6 ITC+thymoquinone, 7 thymoquinone+vitamin C, 8 ITC+resveratrol 9 vitamin C+ITC, 10 ITC+thymoquinone+vitamin C+resveratrol, 11 thymoquinone+resveratrol, 12 vitamin C+resveratrol. Several different incubation times and different concentrations of the molecules are examined to observe the effect of ITC, thymoquinone, vitamin C and resveratrol and the combination thereof.

EXAMPLES

Each of Allyl Isothiocyanate (AITC), Phenyl Isothiocyanate (PEITC), Thymoquinone, or Resveratrol Effectively Induces Cell Death In Vitro The experiments were performed with the following procedure.

A549 cells were plated into 48 well culture plates at a density of $3.0 \times 10^4$ cells/cm$^2$. Cells were dissociated with 0.05% trypsin EDTA following a 5-minute incubation at 37° C., neutralized in a 1:1 ratio of standard medium and counted using a hemocytometer prior to plating. All wells were settled overnight prior to addition of one of the following treatment compounds: AITC, PEITC, Thymoquinone, or Resveratrol. All treatments were performed within 24 hours following initial plating.

Treatment of the A549 cells occurred at the following time points and concentrations: AITC—25 μM, 50 μM and 100 μM for 24, 48 and 96 hours. PEITC—25 μM, 50 μM, 100 μM and 200 μM for 24, 48 and 96 hours. TQ—25 μM, 50 μM, 100 μM and 200 μM for 24, 48 and 96 hours. Resveratrol—25 μM, 50 μM and 100 μM for 48 and 96 hours. DMSO was used to dissolve each compound, and cells treated with DMSO without any of tested compounds served as a control. Treated cells received daily treatments using the same concentrations until the last time point of the experiment.

Apoptosis was detected using the CellEvent Caspase 3/7 green detection kit/assay from Thermofisher Scientific. Cells were incubated with diluted assay reagent for 30 minutes at 37° C. prior to analysis, and imaged by a brightfield and a fluorescent microscopes.

CellEvent Caspase-3/7 Green Detection Reagent is intrinsically non-fluorescent, as the four amino acid peptide (DEVD peptide) inhibits the ability of the dye to bind to DNA. However, following activation of caspase-3/7 in apoptotic cells, the DEVD peptide is cleaved, enabling the dye to bind to DNA and produce a bright, fluorogenic response. The fluorescent emission of the dye ~530 can be observed under a fluorescent microscope.

Figure 1:
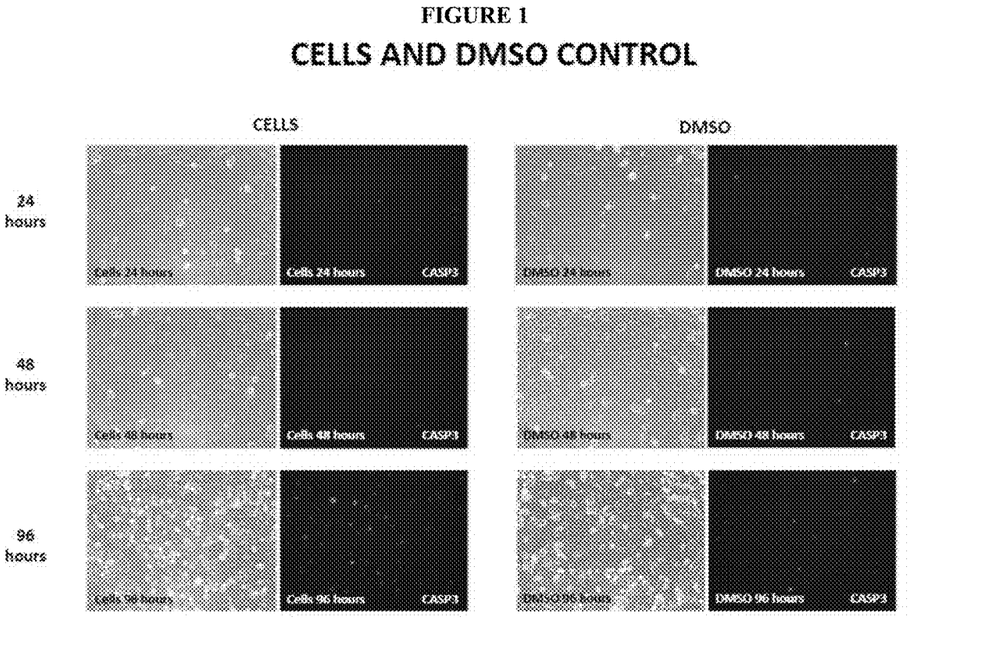
FIG. 1 shows brightfield (left) and fluorescent (right) images of A549 in the absence/presence of DMSO.

FIG. 1 shows a brightfield image on the left and a fluorescent image on the right, corresponding to the same A549 lung cancer cells treated with DMSO. FIG. 2-5 show a brightfield image and a fluorescent image with various time points for various concentrations of the various treatment compounds, AITC, PEITC, Thymoquinone, and Resveratrol.

Figure 2:
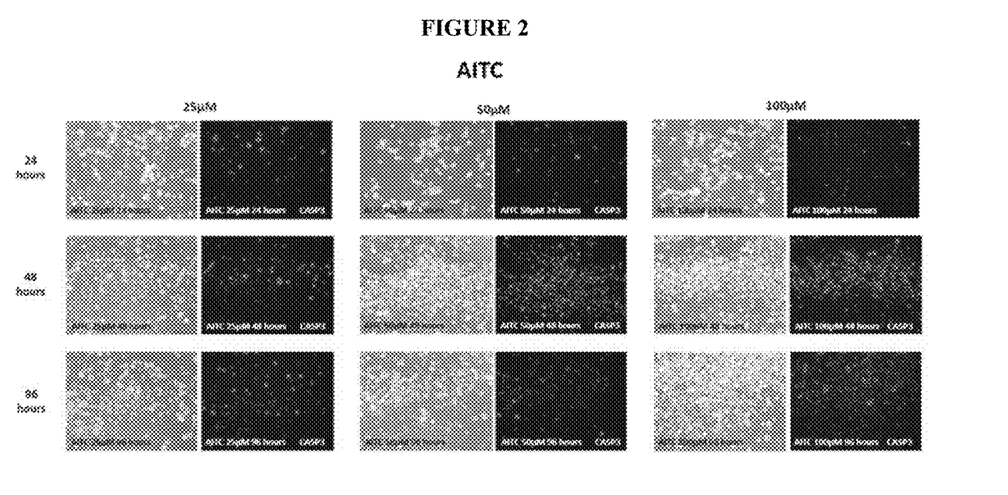
FIG. 2 shows brightfield and fluorescent images of A549 treated with AITC.

FIG. 2 shows that AITC induces cancer cell death. At concentrations 50 μM and higher, more cells are exponentially undergone apoptosis at 48 hours than at lower concentrations. At lower concentrations, cell death was observed to occur at a more gradual rate.

Figure 3:
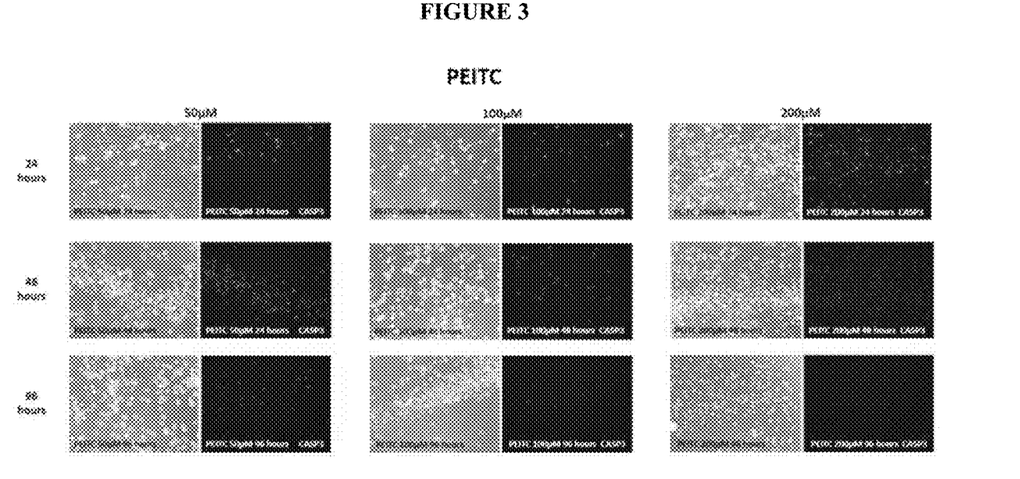
FIG. 3 shows brightfield and fluorescent images of A549 treated PEITC.

FIG. 3 show that PEITC induces cell death. At concentrations 100 μM and higher, more cells are exponentially undergone apoptosis earlier than at lower concentrations. At lower concentrations, cell death was observed to occur at a more gradual rate.

Figure 4:
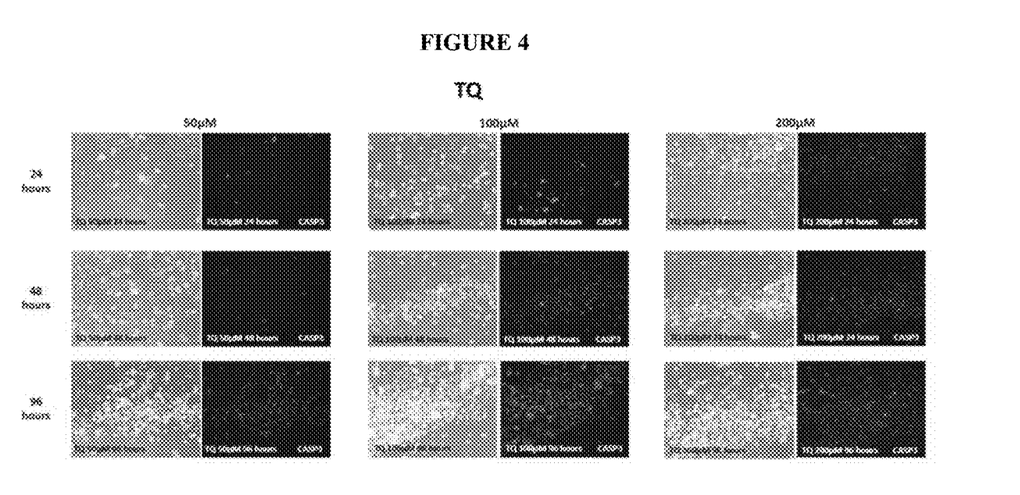
FIG. 4 shows brightfield and fluorescent images of A549 with treated Thymoquinone.

FIG. 4 shows that Thymoquinone induces cell death. At concentrations 100 μM and higher, more cells are exponentially undergone apoptosis earlier than at lower concentrations. At lower concentrations, cell death was observed to occur at a more gradual rate.

Figure 5:
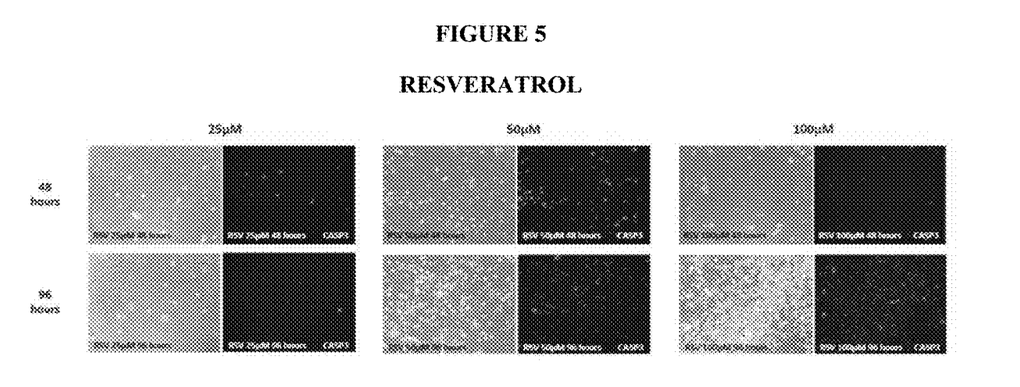
FIG. 5 shows brightfield and fluorescent images of A549 with treated Resveratrol.

FIG. 5 shows that Resveratrol induces cell death. At concentrations 50 μM and higher, more cells are exponentially undergone apoptosis earlier than at lower concentrations. On the other hand, the apoptotic effect was reduced at 25 μM relative to higher concentrations of Resveratrol. It is noteworthy that the apoptotic effects of resveratrol are only observed at 48 and 96 hours, in fact, the effects of the compound are delayed relative to other compounds. After 4 days of treatment, it was observed that each A549 non-small cell lung cancer cell culture that was administered with the either allyl isothiocyanate, phenyl isothiocyanate, thymoquinone, or resveratrol had reached an apoptosis rate of up to 95%.

Figure 6:
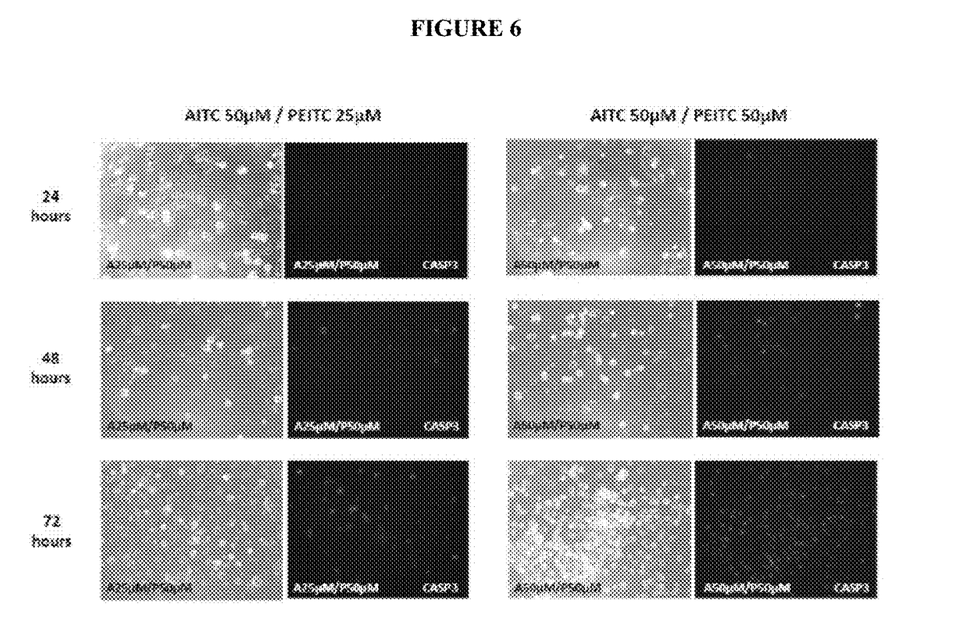
FIG. 6 shows brightfield and fluorescent images of A549 treated with AITC and PEITC.

FIG. 6 shows that the combination of allyl isothiocyanate and phenyl isothiocyanate induces cancer cell death. At concentrations higher than 25 μM phenyl isothiocyanate, exponentially more cells are undergone apoptosis at 48 hours than at lower concentrations. At lower concentrations of phenyl isothiocyanate, cell death occurs at a more gradual rate.

Figure 7:
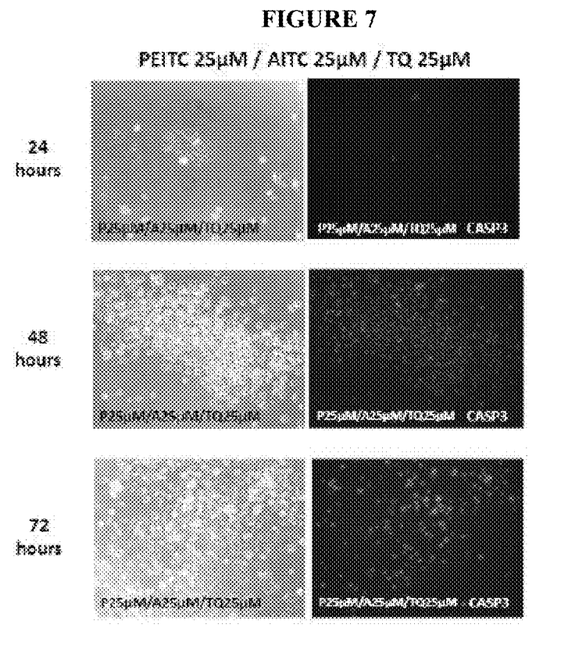
FIG. 7 shows brightfield and fluorescent images of A549 treated with AITC, PEITC, and Thymoquinone.

FIG. 7 shows that the addition of thymoquinone to the previous combination of allyl isothiocyanate and phenyl isothiocyanate induces cancer cell death. At concentrations of 25 µM for all compounds, exponentially more cells are undergone apoptosis at 48 hours than in the cultures without thymoquinone.

Figure 8:
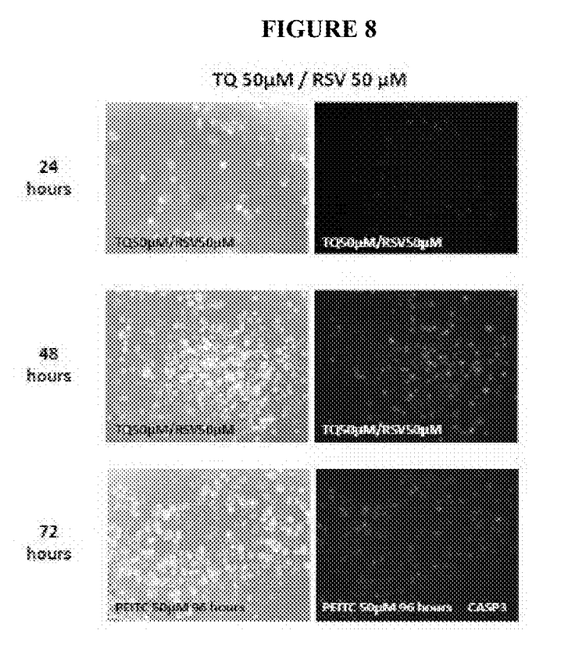
FIG. 8 shows brightfield and fluorescent images of A549 treated with Thymoquinone and Resveratrol.

FIG. 8 shows that the combination of thymoquinone and resveratrol induces cancer cell death. The rate of cell death observed in this combination is similar to the compound combination observed in FIG. 7 which also included thymoquinone. Both appear to exponentially induce apoptosis once they have passed 48 hours.

Figure 9:
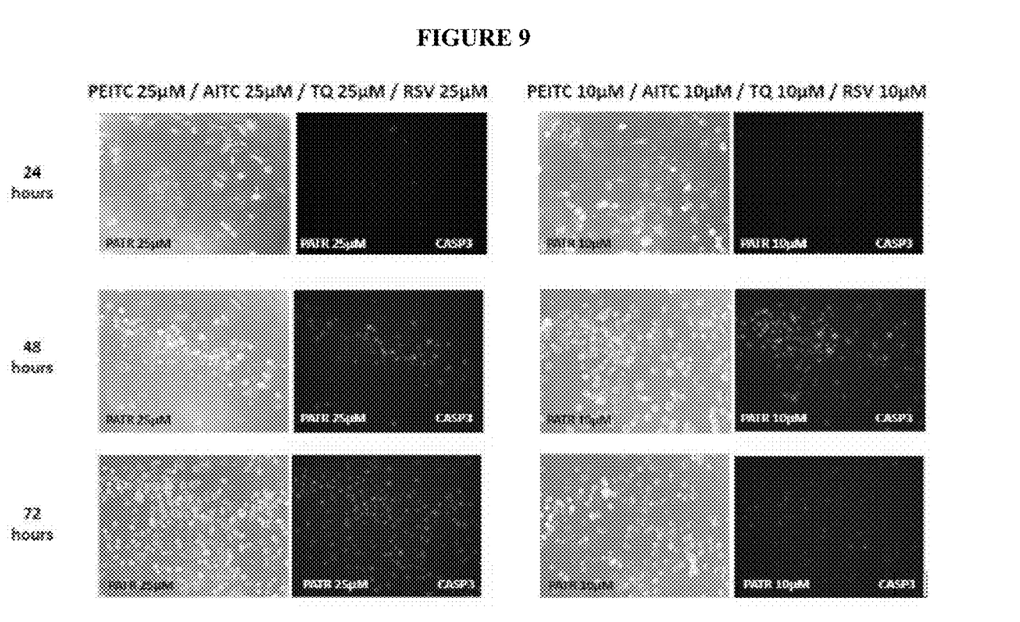
FIG. 9 shows brightfield and fluorescent images of A549 treated with AITC, PEITC, Thymoquinone, and Resveratrol.

FIG. 9 shows that the combination of phenyl isothiocyanate, allyl isothiocyanate, thymoquinone, and resveratrol induces cancer cell death. At concentrations where each compound is higher than 10 µM, exponentially more cells are undergone apoptosis at 48 hours than at lower concentrations. At lower concentrations (<10 µM), the rate of apoptosis appears to be less pronounced.

The combination of compounds (FIG. 6-9) shows that apoptosis is observed at the lowest concentration of 10 µM in a combination including all 4 compounds. A higher degree of apoptosis was observed in the chemical combinations with concentrations higher than 10 µM from a period of 24 to 72 hours (upto 80% apoptosis). Cell apoptosis treated with the combination of compounds is observed upto 72 hours, but not upto 96 hours, as seen in FIGS. 1 to 5, due to the brevity of time. One of reasons is that apoptosis rate of 90% or higher, similar to FIGS. 1-5, could have been reached by 96 hours.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An ingestible product comprising nicotine, (a) isothiocyanate or an isothiocyanate precursor, (b) myrosinase, and (c) resveratrol.

2. The ingestible product of claim 1, formulated as one of the following: a smokeless tobacco, a chewing tobacco, a snuff, a snus, a dissolvable tobacco, a cigarette, a twist, a cigar, and a cigarillo.

3. The ingestible product of claim 1, further comprising powdered tobacco leaf as a source of the nicotine.

4. The ingestible product of claim 1, further comprising a tobacco leaf extract as a source of the nicotine.

5. The ingestible product of claim 1, further comprising at least one of water cress, water cress extract, garden cress, and garden cress extract as a source of the isothiocyanate precursor.

6. The ingestible product of claim 1, wherein the isothiocyanate is synthetic (Phenethyl Isothiocyanate or Allyl Isothiocyanate).

7. The ingestible product of claim 1, further comprising at least one of mustard seed and mustard seed extract as a source of the myrosinase.

8. The ingestible product of claim 1, further comprising thymoquinone.

9. The ingestible product of claim 1, further comprising a black cumin seed extract.

10. The ingestible product of claim 1, further comprising a synthetic vitamin C.

11. The ingestible product of claim 1, further comprising the resveratrol.

12. The ingestible product of claim 1, comprising:
at least one of powdered tobacco leaf and a tobacco leaf extract as a source of the nicotine;
at least one of water cress, water cress extract, garden cress, and garden cress extract as a source of the isothiocyanate precursor; and
mustard seed extract as a source of the myrosinase.

13. The ingestible product of claim 12, further comprising a synthetic isothiocyanate.

14. The ingestible product of claim 12, further comprising thymoquinone.

15. The ingestible product of claim 12, further comprising synthetic vitamin C.

16. The ingestible product of claim 12, further comprising resveratrol.

17. The ingestible product of claim 12, further comprising thymoquinone, resveratrol and a synthetic vitamin C.

18. The ingestible product of claim 1, wherein at least one of the nicotine and the isothiocyanate precursor, synthetic isothiocyanate is encapsulated.

19. The ingestible product of claim 1, wherein the isothiocyanate precursor and synthetic isothiocyanate is encapsulated in at least one of micelles and nano-particles.

20. The ingestible product of claim 1, wherein at least some of the isothiocyanate and precursor and synthetic isothiocyanate is in direct contact with at least one of powdered tobacco leaf and a tobacco leaf extract.

21. The ingestible product of claim 1, wherein the ingestible product includes a filter.

* * * * *